United States Patent
Schildkraut

(10) Patent No.: US 8,486,666 B2
(45) Date of Patent: Jul. 16, 2013

(54) REMOVAL OF THE GUANINE CAP ON THE 5' TERMINUS OF RNA

(75) Inventor: Ira Schildkraut, Boxford, MA (US)

(73) Assignee: New England Biolabs, Inc., Ipswich, MA (US)

( * ) Notice: Subject to any disclaimer, the term of this patent is extended or adjusted under 35 U.S.C. 154(b) by 11 days.

(21) Appl. No.: 13/245,259

(22) Filed: Sep. 26, 2011

(65) Prior Publication Data

US 2012/0077230 A1 Mar. 29, 2012

Related U.S. Application Data

(60) Provisional application No. 61/387,699, filed on Sep. 29, 2010.

(51) Int. Cl.
- *C12P 19/34* (2006.01)
- *C07H 21/02* (2006.01)
- *C07K 14/00* (2006.01)

(52) U.S. Cl.
USPC ................. 435/91.53; 530/350; 536/23.1

(58) Field of Classification Search
None
See application file for complete search history.

(56) References Cited

U.S. PATENT DOCUMENTS

2010/0159526 A1 * 6/2010 Jendrisak et al. ............ 435/91.1

OTHER PUBLICATIONS

Gong et al (Nature Structural & Molecular Biology 18(11): 1297-1299, 2011).*
Sano et al (Ann Neurol 2004;55:241-249).*
Jiao et al (Nature 467: 608-612, published online Aug. 29, 2010).*
Verdier et al (Nucl. Acids Res. 18(23): 7033-7039).*
Print out of web page http://www.neb.com/nebecomm/products/productM0331.asp, retrieved on Aug. 30, 2012.*
Guranowski et al (New J. Chem., 2010, 34, 888-893).*
Lockard et al., Gene Amplification and Analysis, 2:229-251, (1981).
Souliere, et al., Biochemical Journal, 420:27-35, (2009).
LaGrandeur and Parker, The EMBO Journal 17:1487-1496, (1998).
Liu et al., The EMBO Journal, 21:4699-4708, (2002).
Lu, et al., Protein Cell, 2:64-73, (2011).
Salehi, et al., Molecular Microbiology, 46:49-62, (2002).
Jiao, et al., Nature, 467: 608-611, (2010).
Celesnik, et al., Molecular Cell, 27:79-90, (2007).
Deana et al., Nature, 451:355-358, 2008.

* cited by examiner

*Primary Examiner* — Richard Schnizer
(74) *Attorney, Agent, or Firm* — New England Biolabs, Inc; Harriet M. Strimpel

(57) ABSTRACT

Methods and compositions are provided for efficiently removing a guanine cap from the 5' end of an RNA using enzymes. Decapped RNA can be used for cloning, sequencing or other RNA manipulations.

7 Claims, 1 Drawing Sheet

REMOVAL OF THE GUANINE CAP ON THE 5' TERMINUS OF RNA

CROSS REFERENCE

This application claims priority from U.S. provisional application No. 61/387,699 filed Sep. 29, 2010, herein incorporated by reference.

BACKGROUND OF THE INVENTION

Eukaryotic RNA is synthesized with a 5' cap consisting of a guanine nucleotide linked via a 5' to 5' triphosphate linkage to the penultimate nucleotide. In prokaryote, the 5' terminus of a messenger RNA (mRNA) consists of a triphosphate group, without the guanine nucleotide.

The process of 5' capping is required for creating mature mRNA which is then able to undergo translation. Capping enhances RNA stability. In vitro manipulation of the RNA often requires removal of the 5' guanine cap.

Hydrolysis of the triphosphate by chemical means is straight forward, but is not readily controlled and can result in digestion of the entire RNA. Enzymes have been described for removing the 5' cap by selectively hydrolyzing the 5' to 5' triphosphate linkage leaving the remaining RNA intact. Tobacco acid pyrophosphatase (TAP) is the most widely used enzyme at present (Lockard et al., *Gene Amplification and Analysis*, 2:229-251, (1981)). TAP has not been cloned and is difficult to prepare. Other enzymes capable of removing a 5' cap and each having certain limitations include D10 (Souliere, et al., *Biochemical Journal*, 420:27-35, (2009)), Dcp1p (LaGrandeur and Parker, *The EMBO Journal* 17:1487-1496, (1998), Liu et al., *The EMBO Journal*, 21:4699-4708, (2002)), hNUDT16(Lu, et al., *Protein Cell*, 2:64-73, (2011)), Nhm1 (Salehi, et al., *Molecular Microbiology*, 46:49-62, (2002)) and Rai 1 (Jiao, et al., *Nature*, 467: 608-611, (2010)). Except for Rai 1, these enzymes are active only for 5' cap that consists of a 7-methylated guanine nucleotide and not for an unmethylated guanine cap. Moreover, most of these enzymes are difficult to clone. It would be desirable to identify a decapping enzyme that can be easily produced in large quantities, and can remove the guanine cap from an RNA whether it is methylated or unmethylated.

SUMMARY OF THE INVENTION

In embodiments of the invention, methods and compositions are provided as follows:

In one embodiment, a method is provided for removing a guanine cap from the 5' end of an RNA. The guanine cap may include a 7-methylated guanine or an unmethylated guanine and further or alternatively include methylation on one or more of the 2' hydroxy groups of the first 2 ribose sugars of the 5' end of the RNA. The method includes subjecting the RNA to 5' deadenylase (New England Biolabs, Inc., Ipswich, Mass.) or RNA pyrophosphohydrolase (RppH) (New England Biolabs, Inc., Ipswich, Mass.) to remove the guanine cap from the RNA.

In another embodiment of the invention, a mixture is provided that includes a deadenylase or RppH with a guanine capped RNA is provided. The guanine capped RNA may be as large as 1 kb or greater or as small as 2 nucleotides. The deadenylase and/or RppH may be a recombinant enzymes.

DETAILED DESCRIPTION OF THE EMBODIMENTS

Figure 1A:
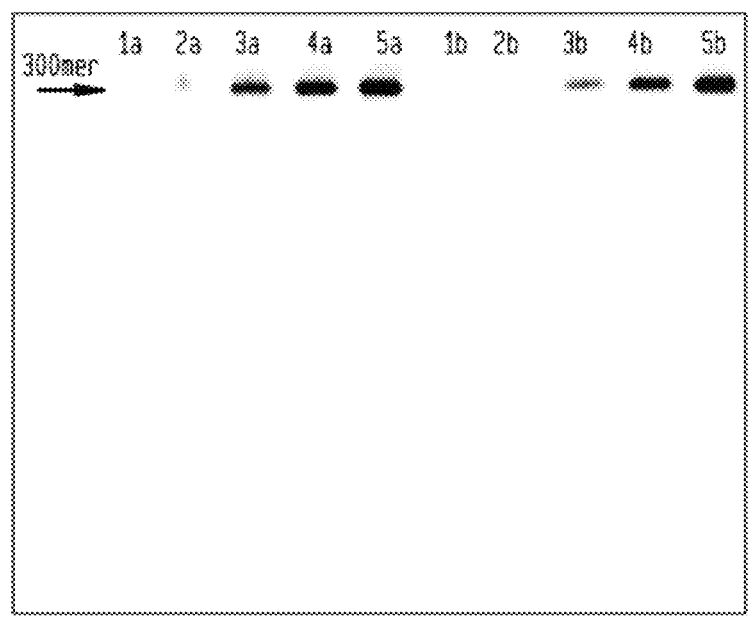
FIG. 1A shows the results of decapping using 5' deadenylase or RppH. 12 µl of the capped RNA (500 ng) was added to 110 µl of 50 mM NaCl, 10 mM Tris-HCl ph 7.9 10 mM MgCl$_2$, 1 mM DTT. To ten µl of the pH 7.9 reaction mixture was added 4 µg (lane 1a), 1.33 µg (lane 2a), 0.33 µg (lane 3a), 0.11 (lane 4a) and no addition (lane 5a) of 5' deadenylase or 2 µg (lane 1b), 0.66 µg (lane 2b), 0.22 µg (lane 2c), 0.07 µg (lane 4b) and no addition (lane 5b) of RppH. The reactions were incubated for 30 minutes at 30° C. 5 µl of each reaction was mixed with 5 µl 95% formamide and heated to 75° C. for 3 minutes. These samples were run on 6% TBE Urea polyacrylamide gel and then imaged as a radiogram.
Figure 1B:
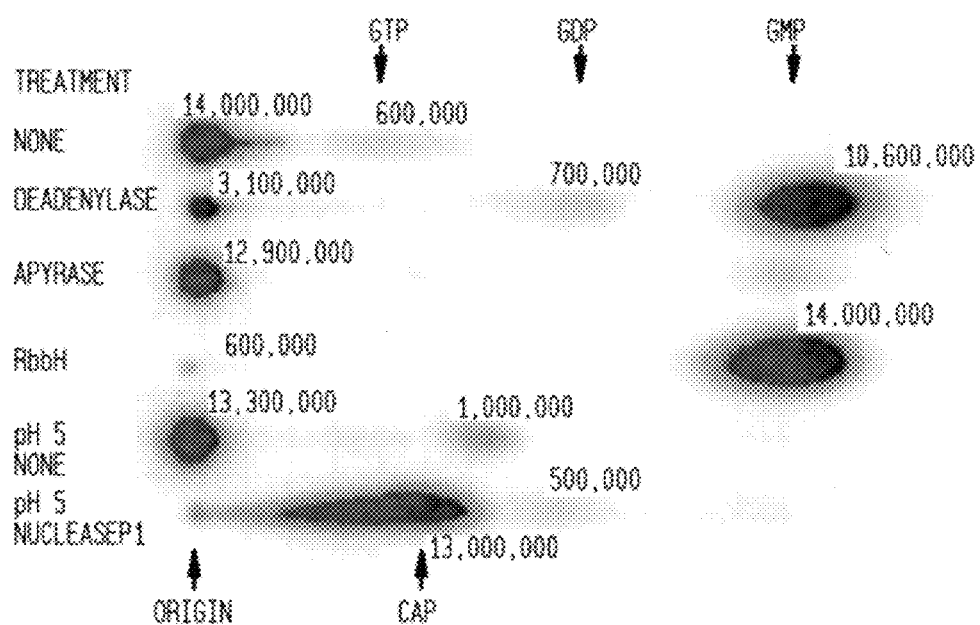
FIG. 1B shows the results of thin layer chromatography as described in the Example. The columns and rows on the TLC are self explanatory.

The 5' deadenylase is capable of deadenylation from 5' end of DNA and RNA, leaving the phosphate at the 5' end. It also cleaves AppppA into ATP and AMP.

RppH (Celesnik, et al., *Molecular Cell*, 27:79-90, (2007)) is found in bacteria such as *E. coli* and *Bdellovibrio Bacteriovorus* and catalyzes the hydrolysis of the triphosphate group on the 5' terminus of RNAs to produce pyrophosphate and RNAs with a monophosphate group on the 5' terminus (Deana et al., *Nature*, 451:355-358, 2008).

We have discovered that 5' deadenylase and RppH function as deguanylases by removing the 5' guanine cap from RNAs.

All references cited herein, as well as U.S. provisional application No. 61/387,699 filed Sep. 29, 2010, are herein incorporated by reference.

EXAMPLE

Adding a Guanine Cap to an RNA

P$^{32}$ alpha-labeled GTP was used in vitro with *S. cerevisiae* capping enzyme complex to cap a 300 mer T7 RNA transcript. The capped-labeled RNA was purified on Ambion megaclear column with 3× ethanol washes.

Removal of the Guanine Cap from the RNA 1) 5 µl of the capped RNA (500 ng) was added to 55 µl of 50 mM NaCl, 10 mM Tris-HCl ph 7.9 10 mM MgCl$_2$, 1 mM DTT. 10 µl of the pH 7.9 reaction mixture was mixed with 2 µg of 5' deadenylase or 1.7 µg of RppH and incubated for 30 minutes at 30° C.

2) 2 µl of RNA was added to 20 µl of 50 mM Na acetate pH 5.5, 0.1 mM ZnCl$_2$. 10 µl of the pH 5.5 reaction mixture was mixed with 3 µl of 250 ng/µl of Nuclease P1 (New England Biolabs, Inc., Ipswich, Mass.) and incubated at 65° C. for 60 minutes.

The reactions were spotted along with appropriate cold markers on PEI cellulose and developed with 0.45 M Ammonium acetate. The results showed that both 5' deadenylase or RppH released the labeled 5' GMP from the capped RNA.

What is claimed:

1. An in vitro method for removing guanosine monophosphate (GMP) or methyl GMP from the 5' end of a capped RNA, the capped RNA comprising GpppN or methylated GpppN, the method comprising
   (a) combining an isolated 5' deadenylase with the capped RNA; and
   (b) removing GMP or methyl GMP from the capped RNA.
2. A method according to claim 1, wherein the guanine cap comprises a 7-methylated guanine.
3. A method according to claim 1, wherein the guanine cap is unmethylated.

4. A method according to any of claims 1 through 3, wherein one or more of the 2' hydroxy groups of the first 2 ribose sugars of the 5' end of the RNA are methylated.

5. An in vitro artificial mixture comprising an isolated 5' deadenylase and a guanine capped RNA.

6. The mixture according to claim 5, wherein the RNA is as large as 1 kb or greater or as small as 2 nucleotides.

7. The mixture according to claim 5 wherein the isolated 5' deadenylase is a recombinant enzyme.

* * * * *